(12) United States Patent
Abrahamson

(10) Patent No.: US 6,801,807 B2
(45) Date of Patent: Oct. 5, 2004

(54) COMMUNICATION SYSTEM AND METHOD FOR COMMUNICATING BETWEEN AN IMPLANTED MEDICAL DEVICE AND ANOTHER DEVICE

(75) Inventor: Hans Abrahamson, Stockholm (SE)

(73) Assignee: St. Jude Medical AB, Järfälla (SE)

(*) Notice: Subject to any disclaimer, the term of this patent is extended or adjusted under 35 U.S.C. 154(b) by 275 days.

(21) Appl. No.: 10/013,247

(22) Filed: Dec. 10, 2001

(65) Prior Publication Data

US 2002/0103514 A1 Aug. 1, 2002

(30) Foreign Application Priority Data

Jan. 31, 2001 (SE) ................................................ 0100284

(51) Int. Cl.⁷ .............................. A61N 1/16; A61N 1/37
(52) U.S. Cl. ........................ 607/60; 128/904; 607/32
(58) Field of Search .............................. 607/2, 30, 32, 607/60; 128/903–904

(56) References Cited

U.S. PATENT DOCUMENTS

| 5,839,075 | A | * | 11/1998 | Haartsen et al. ............. 455/450 |
| 6,150,951 | A | | 11/2000 | Olejniczak ............. 340/825.03 |
| 6,535,766 | B1 | * | 3/2003 | Thompson et al. ........... 607/60 |
| 2003/0088295 | A1 | * | 5/2003 | Cox ........................... 607/60 |

* cited by examiner

Primary Examiner—Carl Layno
(74) Attorney, Agent, or Firm—Schiff Hardin LLP

(57) ABSTRACT

In a medical communication system and method adapted to perform communication between two units, at least one of said units being adapted to be implanted in a human or animal body, having one active channel among a number of communication channels, all of the communication channels are monitored. All channels not presently used for communication between the units, called passive channels, are continuously monitored by the concurrently with the performed communication and the result of this monitoring is stored in a register table provided with one register for each communication channel, the stored information identifying if a channel is available for communication usage.

10 Claims, 2 Drawing Sheets

COMMUNICATION SYSTEM AND METHOD FOR COMMUNICATING BETWEEN AN IMPLANTED MEDICAL DEVICE AND ANOTHER DEVICE

BACKGROUND OF THE INVENTION

1. Field of the Invention

The present invention relates to a medical communication system and method for communicating between an implanted device and another device in the system.

2. Description of the Prior Art

In RF coupled systems, which are perhaps the most commonly employed communication systems in modern implantable device systems, information is transferred from a transmitting coil to a receiving coil with a radio-frequency carrier signal. The carrier signal is modulated with the data that is to be transmitted using an appropriate modulation scheme, such as phase shift keying (PSK), frequency shift keying (FSK), or pulse position modulation (PPM), among numerous others. The modulated carrier induces a voltage in the receiving coil that tracks the modulated carrier signal. This received signal is then demodulated in order to recover the transmitted data. Because the stainless steel or titanium can commonly used to hermetically enclose an implanted device acts as a low-pass filter for the transmitted RF signals, attenuation increases as frequency is increased. Devices currently on the market have a maximum frequency of less than 200-kHz. Also, the transmitting range has been limited to 2 to 3 inches or so.

Depending upon the type of modulation and demodulation used in an RF communication system, the data or bit rate cannot exceed a predetermined fraction of the carrier frequency; otherwise, the ability to reliably distinguish between modulation representing a digital (binary) "1" from a digital "0" is compromised. Schemes are known which encode digital data to transmit more data per unittime and reduce current drain in the implanted device. However, at very high data transmission rates, the current drain would be very high.

RF communication programming units typically interface with the implanted device through the use of a programming head or programming paddle, a handheld unit adapted to be placed on the patient's body over the implant site of the patient's implanted device. In some cases, a magnet in the programming head effects reed switch closure in the implanted device to initiate a communication session (this is a safeguard against accidental programming of the device; otherwise, reed switch closure has little meaning as far as communication of information). Thereafter, uplink and downlink communication takes place between the implanted device's transmitter and receiver and a receiver and transmitter disposed within the programming head.

A newly proposed standard for Medical Implant Communications Service, MICS, states that a number of radio communication channels within a certain frequency range can be used to establish a communication link between an implanted device and an external unit, or between implanted devices. According to the standard one communication link, i.e. communication between two devices, is not allowed to use more than one channel at a time. If a channel becomes unusable of some reason the system can switch to another of the specified channels. Before a new channel can be accessed, the channel shall be monitored in a manner described by the standard in order to avoid collisions.

To avoid accessing a channel in use, a MICS system shall, according to the standard, monitor the channel within the frequency range allocated for MICS information transmission before attempting to establish contact. The earmarked frequency range for communication is divided into N channels. The standard states that a channel shall be monitored for a period of at least 10 ms within 5 seconds prior to access, to ensure it is not occupied. In a noisy environment the channel in use can become inaccessible and a rather frequent channel switching can be necessary due to circumstances beyond the control of the operator.

If a search fails on one channel, e.g. due to too high noise level or if the channel is already in use, a 10 ms search period must be started to monitor a new channel and the procedure must be repeated until a noise-free channel is found. Repetitive searches might result in several 10 ms search periods before a noise free channel is found which lowers the transmission stability of the communication link.

Furthermore, the standard prescribes a procedure how to investigate a channel before accessing it. In short a frequency monitoring is performed by incorporating a mechanism in a medical implant transmitter for monitoring the channel or channels that the MICS system devices intend to occupy. The monitoring system antenna shall be the antenna normally used by the transmitter for a communications session. Before a medical implant transmitter initiates a MICS communication session, the following access criteria must be met:

(1) The monitoring system bandwidth measured at its 20 dB down points must be equal to or greater than the emission bandwidth of the intended transmission.

(2) Within 5 seconds prior to initiating a communications session, circuitry associated with a medical implant transmitter must monitor the channel or channels the MICS system devices intend to occupy for a minimum of 10 milliseconds per channel. Before transmitting on an alternate channel, the channel must be monitored for a period of at least 10 milliseconds.

A similar way of detecting carrier frequencies is also included in a standard draft version from European Telecommunication Standard Institute (ETSI). The European standard covers radio equipment in the frequency range 402 MHz to 405 MHz for Ultra Low Power Active Medical Implants and Accessories. Within this frequency range the maximum permitted emission bandwidth for each channel is set to 300 kHz, i.e. 10 channels side by side starting from 402 MHz.

U.S. Pat. No. 6,150,951 relates to a medical telemetry system with wireless and physical communication channels. The system includes an apparatus for monitoring a transmission activity in a pre-given channel range for determining possible channels in use, so that the transmission channel is assigned to the transmitter in accordance with the determined channels in use. Before a transmitter will be used for transmission purposes in combination with a receiver, the receiver monitors the "on air activity" in its environment for any transmission activity in a certain channel range assigned to the receiver. This phase is called the "scanning phase". The receiver thus determines which channels are in use, e.g., by any other transmitter or by other functional units. The receiver may e.g. include a synthesizer receiver unit for stepping through a predefined channel range and for measuring the received signal strength on each of the channels. When the received signal strength of a certain channel exceeds a certain predefined value, the receiver will treat this channel as being in use. In this known device the transmitter is designated a specific channel during the scanning phase that it then uses during operation. One drawback with this system is that it is unable to handle a situation when e.g.

noise disturbs the used specific channel during operation. The reason is that the scanning phase is performed before the transmitter will be used for transmission purposes.

SUMMARY OF THE INVENTION

An object of the present invention is to provide a technique for communication in a medical system having at least one implanted device that minimizes the time spent to decide which new channel to be used once the currently used channel becomes unusable in order to recognize an available channel for a fast channel switchover.

The above object is achieved in accordance with the principles of the present invention in a medical system having two units, at least one of the units being implanted in a subject, and in a method for communicating between two such units in a medical system, wherein a single channel, from among a number of communication channels, is used to establish a communication link between the two units during a communication time interval, the channel which is in use being an active channel, and the other channels being passive channels, and wherein the passive channels are monitored with regard to their availability for communication during the communication interval, and the result of this monitoring is stored in a register table having respective registers for the communication channels, and wherein the active channel is also monitored during the communication time interval and if the active channel becomes unsuitable for establishing said communication link, an automatic switchover is made to an available passive channel, which immediately then becomes the active channel.

Thus, instead of interrupting the transmission once the current channel is discarded and wasting time during the one or several 10 ms search periods the new channel(s) being monitored the monitoring process runs continuously and concurrently with the normal transmission process.

DESCRIPTION OF THE PREFERRED EMBODIMENTS

Figure 1:
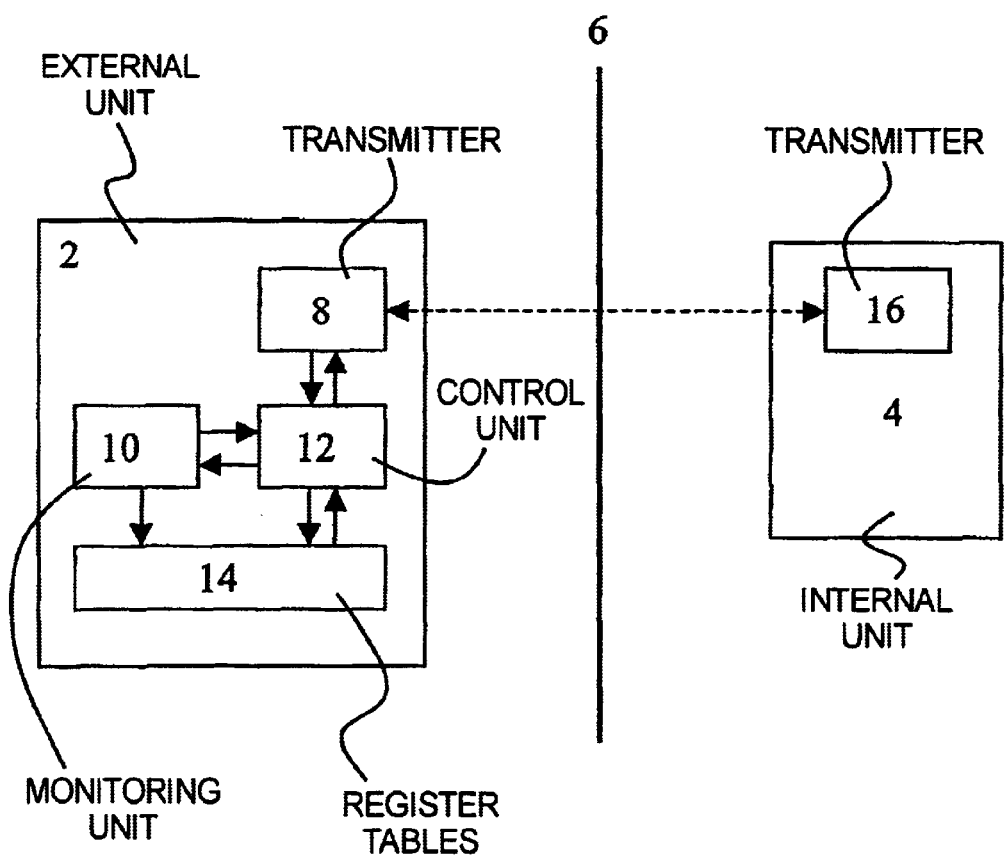
FIG. 1 shows a simplified block diagram of a medical communication system according to the present invention.

The medical communication system shown in FIG. 1 has two units, at least one of which is adapted to be implanted in a human or animal body. FIG. 1 discloses a system comprising an external unit 2 and an internal unit 4 separated by the skin 6 of the patient. The external unit 2 contains a transmitter 8, a monitoring unit 10, a control unit 12 and register tables 14. Naturally many other components are included in the external unit 2, but these are omitted when describing the present invention, as they are not directly involved when practicing the invention. Persons skilled in the art are aware of these other components, among which are energizing means, memory means, display means, data entering means e.g. a keyboard, etc. Also omitted is a programming head, which inter alia includes transmitting coils, used to generate the radio frequency signals. The programming head is connected to the transmitter 8 e.g. via an electrical cable and is positioned during transmission on the skin close to the internal unit 4. Naturally other possibilities are possible, e.g. the programming head need not be positioned in the vicinity of the internal unit and the communication between the programming head and the external emitter may be wireless.

Any conventional programming head adapted for the used radio frequencies may be used.

The internal unit 4 is adapted to be implanted into a human or animal body and includes a transmitter 16 arranged to communicate with the transmitter 8. The internal transmitter 16 is provided with all necessary circuitry in order to be able to perform the communication, e.g. a transmitting antenna, modulation and demodulation means.

The internal unit 4 may be any device adapted to be implanted into a human or animal body, e.g. a heart pacemaker, a heart defibrillator, a cardioverter or an infusion pump, and is naturally provided with the necessary means needed to perform its intended purpose. In case of a heart pacemaker the internal unit includes a battery means, pulse generating means, electrode means, control means etc.

In FIG. 1 the dotted double-arrowhead line designates the radio frequency communication signal between the units 2 and 4.

Using one active channel of a number of radio communication channels e.g. in accordance with the above-described MICS system performs the communication between the two units 2 and 4.

According to the present invention the monitoring unit 10 monitors all communication channels in the prescribed frequency range not presently used for communication between the units, i.e. the passive channels. These channels are continuously monitored by the monitoring unit 10 concurrently with the performed communication.

During the monitoring the monitoring unit 10 preferably uses the antenna, e.g. the programming head, connected to the transmitter 8.

The purpose of the monitoring is to assess the activity in channel using a specific frequency. The activity may be caused by the channel already being used or by any type of interference, e.g. noise due to electromagnetic interference.

When the activity in the monitored channel is too high that channel is regarded as non-available for communication. The activity of a specific channel may be determined in many different ways. One way is to integrate the signal in the frequency designated to the channel and to compare the calculated value with a threshold. If the value is below the threshold the activity is low and the channel is available for communication. If the value is above the threshold the activity of the channel is considered too high to allow secure communication. The result of the monitoring is stored in the register table 14, that is provided with one register for each communication channel. In each register may be stored information reflecting the result of the monitoring, either as a logic value, e.g. OK or not OK for communication, or the analog value resulting from the integration. Alternatively both these values may be stored.

When switching to a new channel the control unit 12 that initiates the switching may either use a simple criterion that the activity level shall be lower then a threshold, i.e. choose one of the channels having an OK stored in its register. Alternatively the channel is chosen that has the lowest analog value stored in the register table, provided that this value is below the threshold. Upon channel switching one of the passive channels that fulfils the above-mentioned criterion becomes active and the presently active channel becomes passive. The channel switching according to the present invention is more or less instantly performed and depends upon which channel switching method that is presently used.

In one channel switching method the messages sent from a transmitter to a receiver includes information about which channel/channels the receiver should switch to. The channel switching is performed either in response to a direct switching command, in response to a command included in the message, or the receiver itself changes to a defined channel if the connection to the transmitter is broken.

Alternatively the transmitter and receiver have a predefined channel switching scheme to follow as soon as a channel switching takes place. Thus, if the receiver does not receive a message within a prescribed time or does not receive confirmation of the last sent message the receiver switches to the next predefined channel, naturally provided that the next predefined channel is available for communication.

According to a preferred embodiment of the present invention all passive channels are monitored for a period of at least 10 ms at least every $5^{th}$ second.

The minimum time set for monitoring and the frequency of the monitoring are dependants of requirements set by different standards that of course may be changed, e.g. to a shorter monitoring period and a more frequent monitoring.

According to a first preferred embodiment of the present invention the passive channels are monitored using a first monitoring mode where all passive channels are scanned in sequence, wherein each channel is at least scanned each $5^{th}$ second.

According to a second preferred embodiment of the present invention the passive channels are monitored using a second monitoring mode where all passive channels are monitored in parallel.

According to a third preferred embodiment of the present invention the passive channels are monitored using a third monitoring mode where all passive channels are monitored in parallel by using a frequency analyzing algorithm. In this embodiment a wide-band signal is created from the received radio signal with a bandwidth equal to the sum of the bandwidths of all N channels. After applying a frequency analyzing algorithm, such as the Fast Fourier Transform or a wavelet algorithm, the signal level in all N channels can be calculated simultaneously in one single process. The corresponding activity level in each channel, resulting from the calculation, is then stored in the register table in the same way as described above. The wavelet algorithm is a method for determining the frequency content in an unknown signal by adapting known signals having known frequency contents to the unknown signal so that the unknown signal may be expressed in terms of the known signals.

When choosing a new active channel different selection criterion may be used when activity information is stored in the register table 14 in the form of OK or not OK.

According to one selection criterion the channel that last received an OK is chosen. According to another selection criterion the channel using a frequency that differs most from the frequency of the presently used active channel is chosen. Naturally combinations of these criteria may be used.

As indicated above each unit has communication means e.g. transmitter coils, adapted to transmit and receive information using the communication channels.

Figure 2:
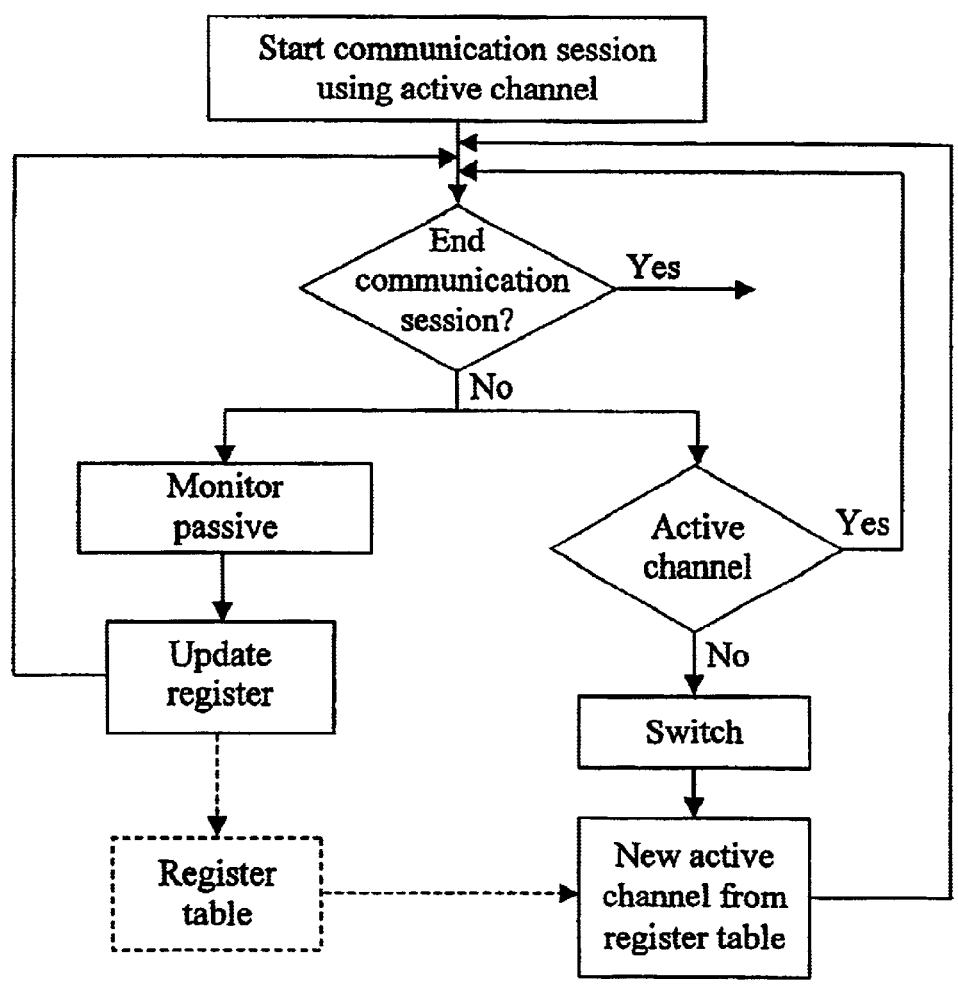
FIG. 2 shows a flow chart illustrating a method in the medical communication system according to the present invention.

FIG. 2 shows a flow chart schematically illustrating a method in the medical communication system according to the present invention.

The illustrated method includes the following main steps or procedures:

a) Start a communication session between two units, using one active channel of a number of radio communication channels. At least one of said units is adapted to be implanted in a human or animal body.

b) Continuously monitoring the communication channels not presently used for communication, called passive channels, by using the monitoring unit 10 concurrently with the performed communication (shown in the left branch of FIG. 2).

c) Storing the result of the monitoring in the register table 14 provided with one register for each communication channel, wherein the result indicates if a channel is available for communication.

FIG. 2 further illustrates (in the right branch) that the active channel is continuously monitored and that a channel switching is performed if it is determined that the active channel is unusable. Upon channel switching one of the passive channels available for communication instantly becomes active.

According to a preferred embodiment each one of the passive channels is monitored in step b) for a period of at least 10 ms at least every $5^{th}$ second.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical communication system comprising:

two units, at least one of said units being adapted for implantation in a subject;

a transmitter/receiver arrangement disposed in said two units, said transmitter/receiver arrangement having a plurality of communication channels, any of which can be active, as an active channel, for establishing a communication link between said two units during a communication time interval, with a remainder of said communication channels being passive channels;

a monitoring unit connected to said transmitter/receiver arrangement in one of said units for monitoring said plurality of communication channels during said communication time interval with regard to respective availability of the communication channels for establishing said communication link, said monitoring unit generating a monitoring result for each of said passive channels and also monitoring said active channel to determine a suitability of said active channel for maintaining said communication link during said communication time interval;

a register table having a plurality of registers in which the monitored results for the respective communication channels are stored; and a control unit connected to said register table and to said transmitter/receiver arrangement for, if said active channel becomes unsuitable for use for establishing said communication link during said communication time interval, immediately consulting said register table to select and substitute one of said passive channels for use as said active channel.

2. A medical system as claimed in claim 1 wherein said monitoring unit monitors each of said passive channels for a period of at least 10 ms at least at every fifth second.

3. A medical system as claimed in claim 1 wherein said monitoring unit comprises, for monitoring said passive channels, circuitry means for scanning said passive channels in sequence, with each channel being scanned at least every-fifth second.

4. A medical system as claimed in claim 1 wherein said monitoring unit comprises means for monitoring all of said passive channels in parallel.

5. A medical communication system as claimed in claim 1 wherein said monitoring unit monitors all of said passive channels in parallel using a frequency analyzing algorithm.

6. A medical communication system as claimed in claim 1 wherein said monitoring unit generates an acknowledgment signal, as said monitor result, when a channel among said plurality of channels fulfills a predetermined access criterion, and causes said acknowledgment signal to be stored in the respective register in said register table for the channel which fulfilled the predetermined access criterion.

7. A medical system as claimed in claim 6 wherein said monitoring unit determines that a channel fulfills said access criterion if an energy content of signal activity in the channel is lower than a predetermined value.

8. A medical system as claimed in claim 7, wherein said monitoring unit comprises means for monitoring said energy content by integrating said signal activity.

9. A method for communicating between two units in a medical system, one of said units being adapted for implantation in a subject, comprising the steps of:

initiating a communication session between said two units, using one active channel among a plurality of communication channels, with a remainder of said communication channels being passive channels;

monitoring said active and passive channels during said communication session to determine a continued suitability of said active channel for establishing a communication link and for determining an availability of said passive channels for use in establishing said communication link, thereby obtaining a plurality of measurement results respectively for said channels;

storing said monitoring results in a register table having a plurality of registers respectively for said channels; and if said active channel becomes unsuitable during said communication session for establishing said communication link, immediately consulting said register table to select one of said passive channels available for use in establishing said communication link and substituting said one of said passive channels in place of said active channel, so that said one of said channels becomes said active channel.

10. A method as claimed in claim 9 comprising monitoring each of said passive channels in said communication session for a period of at least 10 ms at least every fifth second.

* * * * *